United States Patent [19]

Demarest et al.

[11] Patent Number: 5,477,609
[45] Date of Patent: Dec. 26, 1995

[54] NEEDLE AND SUTURE SWAGING STATION

[75] Inventors: David Demarest, Parsippany; Robert B. Duncan, Bridgewater, both of N.J.; William Rattan, Cerritos, Calif.

[73] Assignee: Ethicon, Inc., Somerville, N.J.

[21] Appl. No.: 181,599

[22] Filed: Jan. 13, 1994

[51] Int. Cl.⁶ .................................................. B23P 21/00
[52] U.S. Cl. ...................... 29/788; 29/243.517; 53/118; 83/153; 83/950
[58] Field of Search .................................. 606/224, 225, 606/226; 163/1, 5; 53/118, 138.1, 244, 253, 329, 430; 83/151, 153, 950; 206/63.3, 227; 29/243.5, 243.517, 283.5, 515, 516, 517, 564.6, 705, 711, 715, 783, 785, 786, 788, 792, 793, 796, 818

[56] References Cited

U.S. PATENT DOCUMENTS

| | | |
|---|---|---|
| 3,611,551 | 10/1971 | Shave et al. . |
| 3,980,177 | 9/1976 | McGregor . |
| 4,072,041 | 2/1978 | Hoffman et al. . |
| 4,672,871 | 6/1987 | Gudmestad ............................ 83/153 |
| 4,722,384 | 2/1988 | Matsutani . |
| 4,806,737 | 2/1989 | Coates . |
| 4,832,025 | 5/1989 | Coates . |
| 4,922,904 | 5/1990 | Uetake et al. . |
| 5,226,336 | 7/1993 | Coates . |

FOREIGN PATENT DOCUMENTS 212027 9/1988 Japan ......................................... 163/1

Primary Examiner—David P. Bryant
Attorney, Agent, or Firm—Scully, Scott, Murphy & Presser

[57] ABSTRACT

A swaging station incorporates a drawing tower that automatically draws, cuts, and inserts an indefinite length strand of suture material within the suture receiving end of a surgical needle for swaging thereof. The suture receiving end of the surgical needle is positioned within a swaging assembly located at the top of the drawing tower that comprises a first fixed swage die and a second movable swage die forming a swage die opening for positively gripping the suture receiving end of the needle positioned therein. A first suture alignment die and a second suture alignment die are precisely registered below and adjacent the respective first and second swage dies to form a lower funnel guide that is axial with the swage die opening for positioning the tip of the suture strand therein. The lower funnel guide has an exit diameter that is larger than the diameter of the suture tip and smaller than the diameter of the suture receiving end of the needle for easy placement of the suture tip therein. Subsequently, the second movable swage die is actuated to swage the suture tip to the needle.

25 Claims, 14 Drawing Sheets

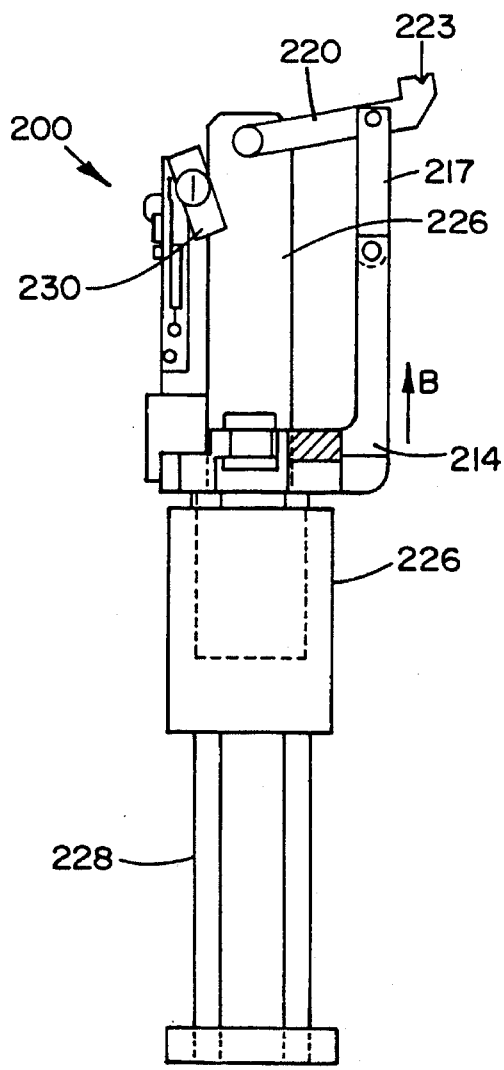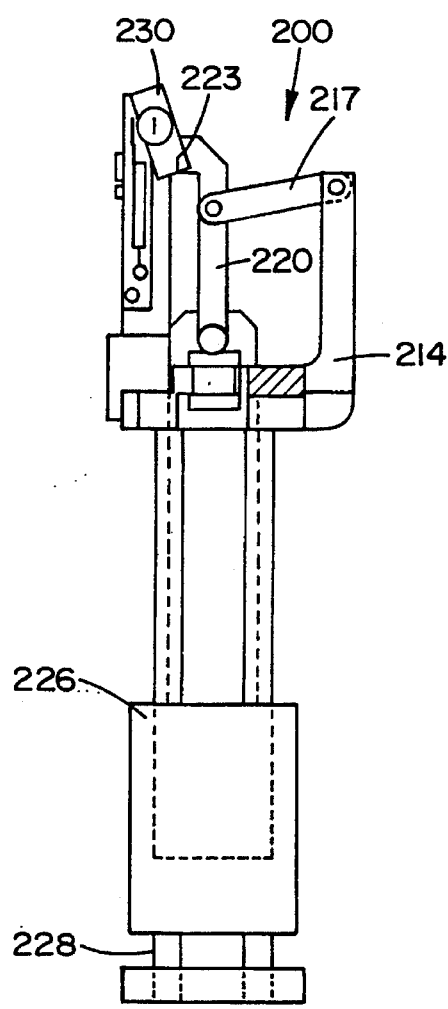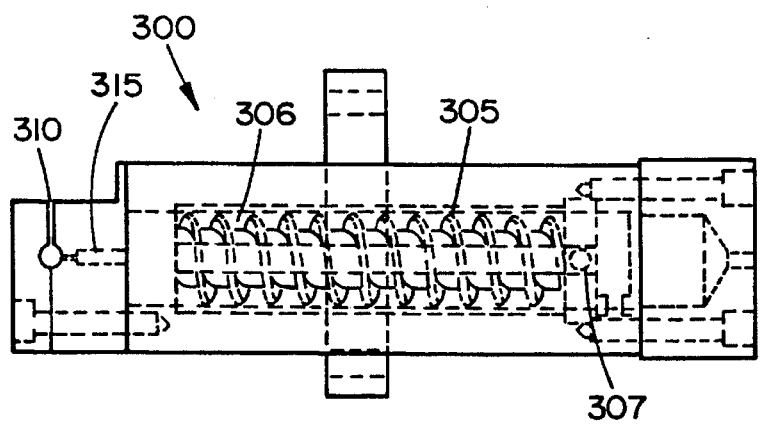
FIG.6   FIG.7
FIG.8

NEEDLE AND SUTURE SWAGING STATION

FIELD OF THE INVENTION

The present invention relates generally to machines for automatically threading needles, such as surgical needles and the like, and more specifically, to an apparatus for automatically swaging a length of suture material to a surgical needle.

DESCRIPTION OF THE PRIOR ART

The medical products industry presently utilizes semi-automated procedures for swaging sutures to surgical needles. For instance, as described in U.S. Pat. No. 3,611,551, manual intervention is required by an operator to accurately position a suture within the suture receiving opening formed in the surgical needle to accomplish swaging thereof. This process is costly in terms of man-hour labor and efficiency because of the manual manipulations involved.

Presently, suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to change the rack each time a different length of suture is desired.

In U.S. Pat. No. 4,922,904, the suture material is supplied wound on a bobbin and is fed through various guide means and a heater for straightening the material, prior to insertion within the crimping cavity of the surgical needle. In one embodiment shown therein, an elaborate television monitoring means is required for aligning the drawn suture within the crimping cavity of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is additionally fed a predetermined distance prior to cutting to obtain a suture strand of predetermined length. Thus, to obtain uniform lengths of suture material every time requires careful manipulations and precise controls, and the processes used to accomplish these tasks are also costly in terms of man-hour labor and efficiency.

It would be far more desirable to provide a suture cutting system and swaging apparatus that is fully automated and which can automatically cut uniform lengths of suture material at high-speeds.

It would also be highly desirable to provide a suture cutting system that can accurately position suture material within the confines of the suture receiving openings of surgical needles at an appreciable rate and without elaborate techniques or manual intervention.

Also desirable would be to provide a suture cutting system and swaging system that is operable under the control of a control system computer that can provide automatic adjustments to the positions of swage dies when different size sutures are swaged to various sized surgical needles, and, to adjust for variations when swaging needles of like size.

SUMMARY OF THE INVENTION

Accordingly, it is an object of the instant invention to provide a needle threading and swaging station for automatically drawing, cutting, and inserting the tip of a length of suture material within the ends of a surgical needle for swaging thereof.

It is another object of the instant invention to provide a cost-effective automatic needle threading and swaging station that virtually eliminates operator exposure to repetitive manual operations.

Furthermore, it is an object of the present invention to provide a needle threading and swaging station, wherein the needle is automatically indexed to the swaging station prior to suture insertion and swaging thereof.

Moreover, it is an object of the present invention to provide a needle threading and swaging station that performs one operation consisting of drawing an indefinite length strand of suture material, heating the strand to stiffen a tip thereof, cutting the strand at a predetermined length, and swaging the suture to a surgical needle at the rate one needle per second.

These and other objects of the present invention are attained with a swaging station that incorporates a drawing tower that automatically draws, cuts, and inserts an indefinite length strand of suture material within the suture receiving end of a surgical needle for swaging thereof. The suture receiving end of the surgical needle is positioned within a swaging assembly located at the top of the drawing tower and comprising a first fixed swage die and a second movable swage die forming a funnel shaped swage die opening for positioning of the suture receiving end of the needle therebetween. A first fixed suture alignment die and a second movable suture alignment die forms a lower invertedly tapered alignment guide therebetween and axial with the upper alignment guide for positioning the tip of the suture strand therein. The lower alignment guide has an exit diameter that is larger than the diameter of the suture tip and typically equal or smaller than the diameter of the suture receiving end of the needle to enable accurate placement of the suture tip therein. Subsequently, the movable swage die is actuated under controlled air pressure to swage the suture tip to the needle.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 6 is a detailed top view of the cutter assembly 200 shown in a fully retracted position.

FIG. 7 is a detailed top view of the cutter assembly 200 shown in a fully extended (cutting) position.

FIG. 8 is a detailed top view of the tipping assembly 300 for heating a portion of the suture material.

FIG. 12(a) is cut away top view of the cam dial plate 110 showing cam follower 165a in a retracted position within cam track 182a.

FIG. 12(b) is cut away top view of the cam dial plate 110 showing cam follower 165a in an extended position within cam track 182a.

DETAILED DESCRIPTION OF THE PREFERRED EMBODIMENT

Figure 1:
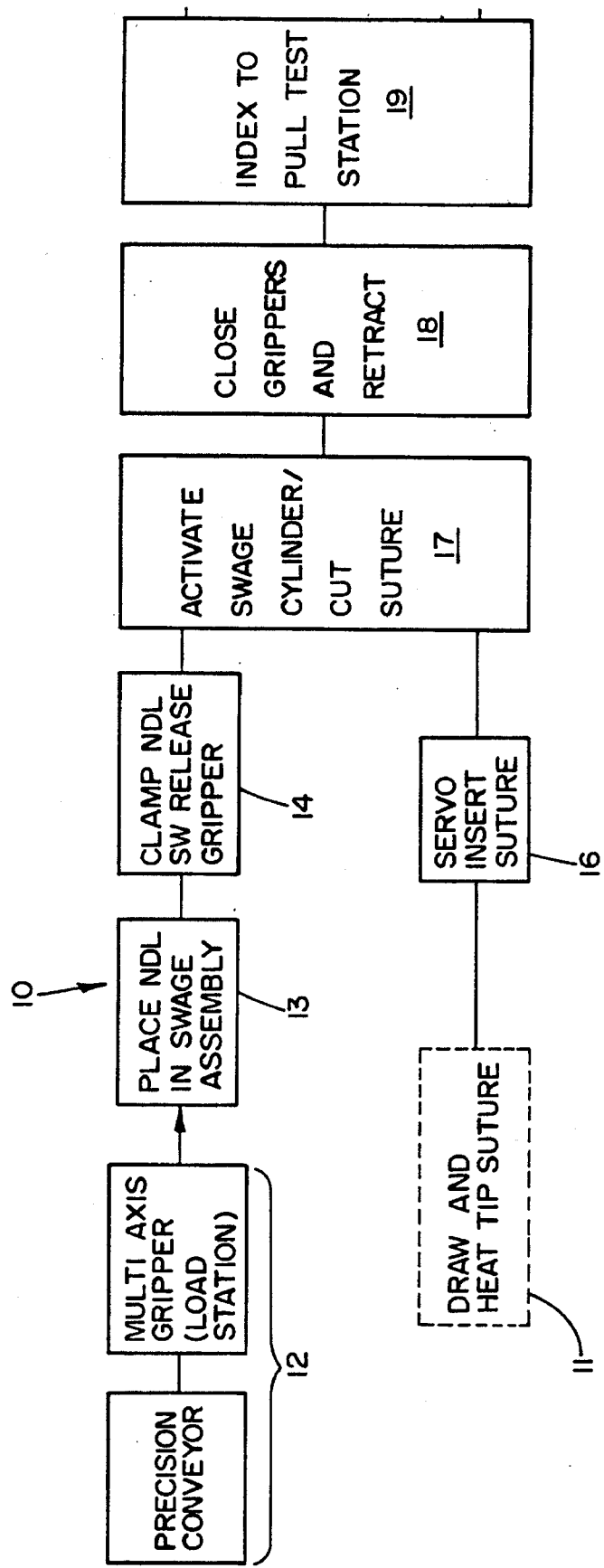
FIG. 1 is a block diagram showing the process flow for the needle threading and swaging system of the present invention.

FIG. 1 is a block diagram generally illustrating the system 10 used to automatically draw an indefinite length of suture material for cutting a predetermined length thereof, and to automatically insert the cut suture within a suture receiving end of a surgical needle for automatic swaging thereof. The entire process takes place at a swaging station which comprises an apparatus used to draw and cut an indefinite length strand of suture material to a uniform length and insert the tip thereof within the suture receiving end of a surgical needle prior to swaging as described in copending patent application U.S. Ser. No. 08/181,595, entitled "R.S.O. Suture Cutting Station" assigned to the same assignee of the present invention and incorporated by reference herein.

In the automatic needle threading and swaging process 10 shown in FIG. 1, surgical needles are individually loaded from a precision conveyor or any suitable means, onto a multi-axis gripper located on a rotary swage dial as indicated as step 12 and described in detail in copending patent application U.S. Ser. No. 08/181,598, entitled "Needle Threading Swedging System" assigned to the same assignee of the present invention. The rotary swage dial is indexed so that the multi-axis gripper positions the needle in a precisely oriented position between two swaging dies of a swage assembly which is indicated as step 13 in FIG. 1. At the same time, an indefinite length of suture strand is drawn from a king spool along a single axis of a drawing tower and a tip thereof is stiffened and registered for insertion within the suture receiving end of the needle, as shown as step 11 in FIG. 1. Next, at step 14, the multi-axis gripper releases its grip on the needle placed between the opening formed by the swaging dies. At the same time the gripper assembly at the drawing tower inserts the tip of the suture strand within the lower invertedly tapered alignment guide to position the tip within the suture receiving end of the needle, as shown as step 16. Next, at step 17, the swage cylinder is activated to automatically swage the suture strand to the needle while a cutting assembly simultaneously cuts the indefinite length of suture strand to a predetermined length. While retaining the armed needle, the multi-axis gripper is then retracted on the swage dial as shown as step 18. Finally, the armed needle is indexed to a pull-test station at step 19 where minimum pull testing and/or destructive pull testing may be performed. A detailed explanation of the apparatus used to carry out each step will be explained in further detail hereinbelow.

The Drawing Tower

Figure 2A:
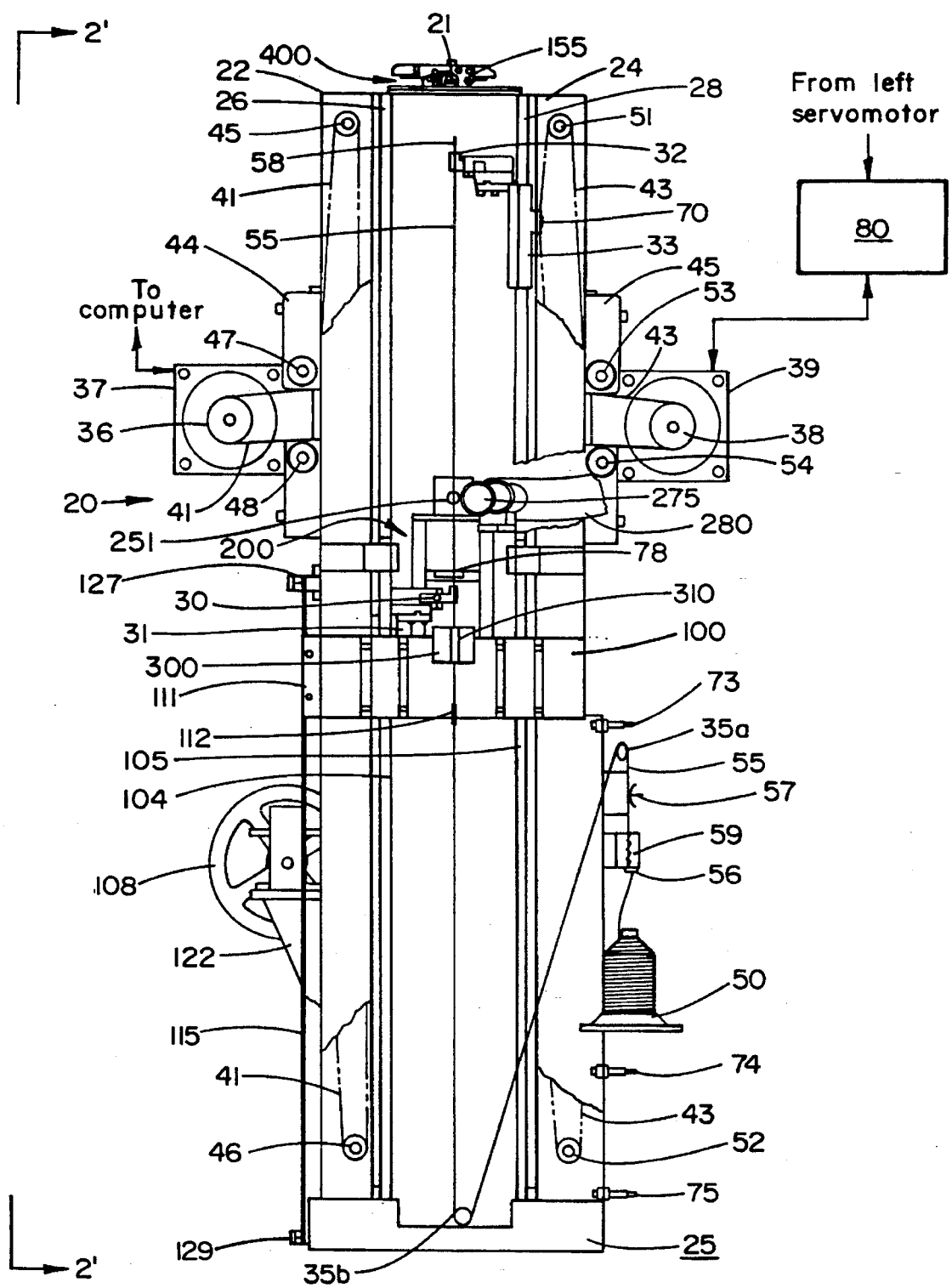
FIG. 2(a) is a detailed view of the servo tower 20 illustrating cutter assembly 200 and heater assembly 300 mounted on tip and cut carrier 100, and a registered multi-axis gripper 155 carrying needle 21 that is positioned for receiving the suture strand within the suture receiving end thereof.
Figure 4:
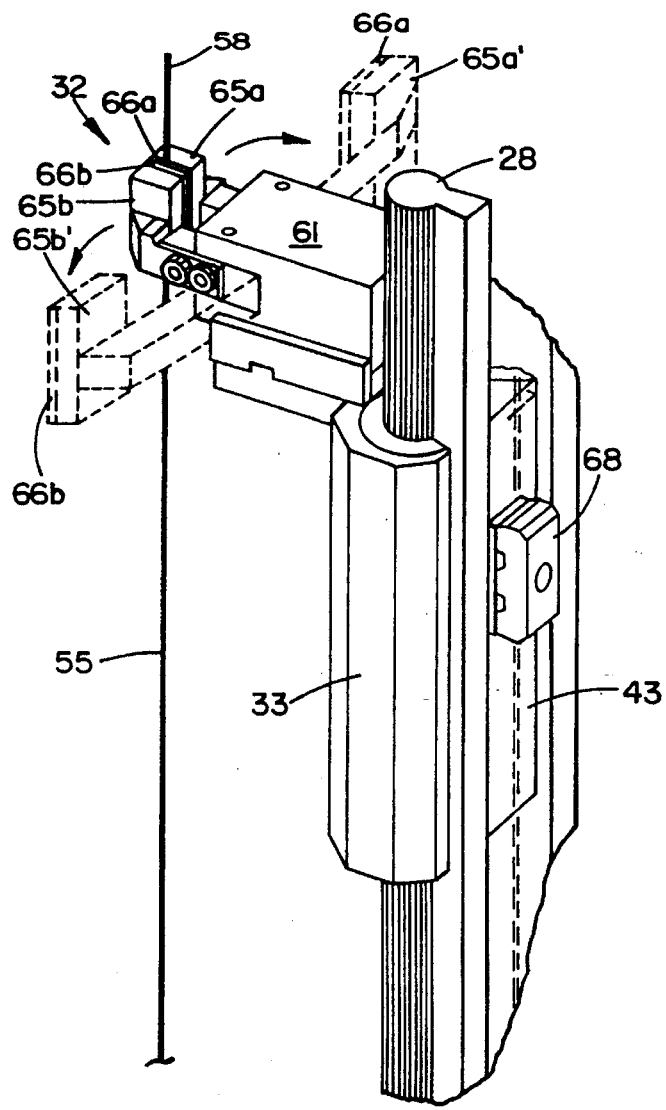
FIG. 4 is an enlarged view of a gripper assembly having gripper arms shown in their closed (suture gripping) and open positions.

A payoff assembly for accomplishing the task of automatically drawing an indefinite length suture material is embodied as a drawing tower 20 shown in FIG. 2(a). The drawing tower 20 comprises left side rail and right side rail 24 mounted on suitable mounting block 25 and defining a drawing bed for drawing an indefinite length of suture material along a drawing axis therebetween. Located parallel to the left and right side rails 22,24 and suitably connected thereto are respective left guide rod 26 and right guide rod 28. The first gripper means or right gripper 32 reciprocates up and down along right guide rod 28 while the second gripper means or left gripper 30 reciprocates up and down the left guide rod 26. Each of the grippers 30,32 grip the suture material that is fed from a spool through pulley 35 located at the bottom of the drawing tower 20, and carries the material to the upper end of the tower. The right gripper 32 is mounted on right gripper carrier 33 for vertical movement along right guide rod 28, and the left gripper 30 is mounted on left gripper carrier 31 for vertical movement along left guide rod 26 as shown in FIG. 2(a). FIG. 4 illustrates a gripper 32 (and 30) having a gripper arm drive 61 that is pneumatically operated to drive pair of retractable gripper arms 65a, 65b toward each other to a suture gripping position, or, away from each other to an open position. Each retractable gripper arm is provided with a resilient, nonmetallic pad 66a, 66b for gripping the suture material 55 at a free end thereof when actuated to the gripping position. To release the grip of the suture, gripper arms 65a,65b are retracted approximately 180 degrees apart in the direction indicated by the arrows of FIG. 4 to the open position. When in the open position the gripper arms 65a', 65b' do not interfere with the motion of the other vertically moving gripper as it reciprocates along the respective left or right rod, nor will it interfere with the cutter assembly 200 that cuts the strand to a predetermined length as will be explained below. The retractable nature of the grippers and of the cutting assembly enables single drawing axis operation.

Figure 2B:
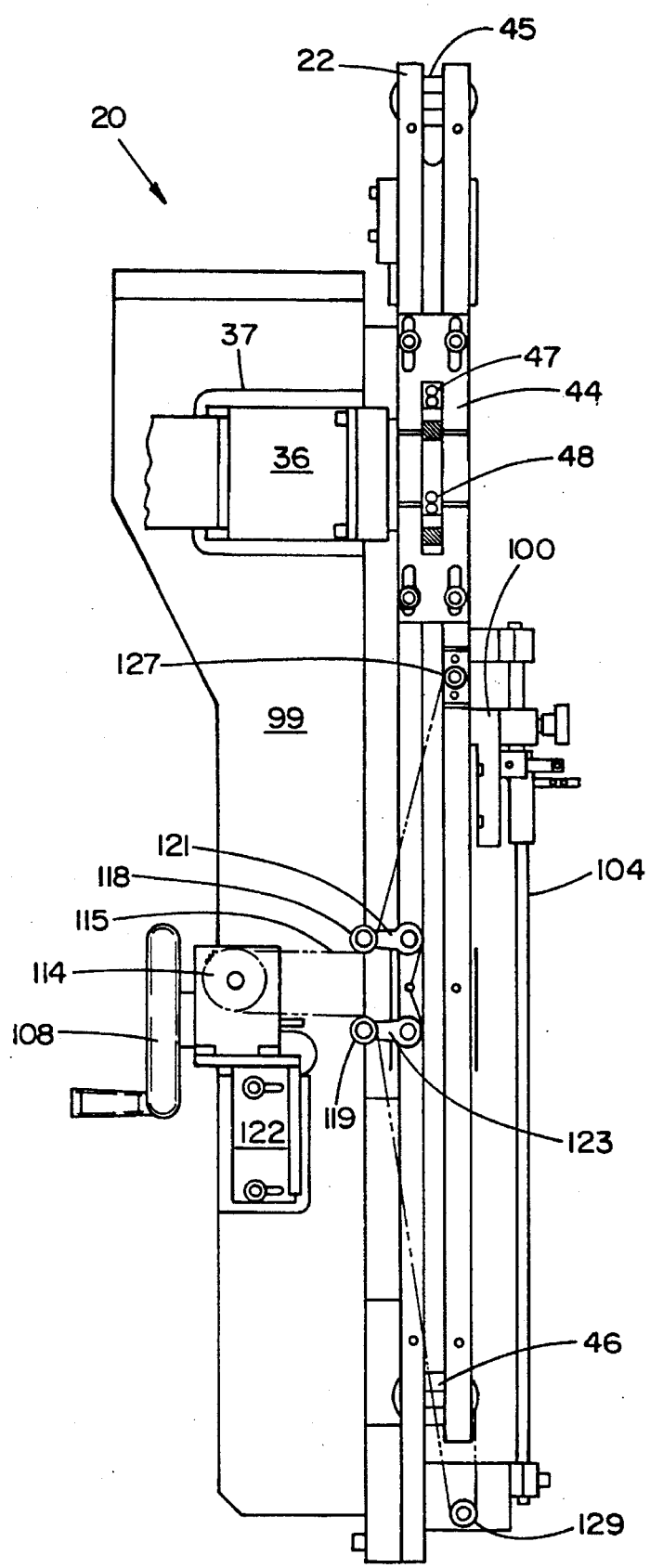
FIG. 2(b) is a detailed side view of the cutting assembly taken along line 2'–2' of FIG. 2(a) showing the pulley assembly for moving tip and cut carrier assembly 100 of the instant invention.

As mentioned above, each gripper carrier and gripper thereof is designed to advance vertically along the respective left and right rods. As shown in FIG. 2(*a*), the right gripper 32 and gripper carrier 33 is driven by right servo motor 38 which is mounted to the right side rail 24 by right motor mounting bracket 39. Similarly, the left gripper 30 and gripper carrier 31 is driven by left servo motor 36 which is mounted to the left side rail 22 by left motor mounting bracket 37. In the preferred embodiment, both left and right servo motors are interfaced with and controlled by a control system computer, indicated generally as numeral 80 in FIG. 2(*a*), and as explained in further detail in copending patent application U.S. Ser. No. 08/181,607, entitled "Control System" assigned to the same assignee of the present invention. As shown in FIG. 2(*a*), right servo motor 38 drives timing belt 43 which consequently enables vertical positioning of right gripper carrier 33 along right rod 28, while the left servo motor 36 drives timing belt 41 which consequently enables vertical positioning of left gripper carrier 31 along left rod 26. As FIG. 4 illustrates, timing belt 43 is clamped to its respective gripper carrier 33 by a timing belt clamp 68 located on the back of the gripper carrier. A similar timing belt clamp (not shown) is provided on gripper carrier 31 for clamping timing belt 41 to enable vertical movement of gripper 30. FIG. 2(*a*) shows timing belt 41 engaging upper left pulley 45 and lower left pulley 46 as well as idler pulleys 47,48 which are part of tensioner block 44 that adjusts the tension of the timing belt 41 and consequently of left gripper carrier 31. Likewise, FIG. 2(*a*) shows timing belt 43 engaging upper right pulley 51 and lower left pulley 52 as well as idler pulleys 53,54 which are part of tensioner block 45 that adjusts the tension of the timing belt 43 and consequently of right gripper carrier 33.

FIG. 2(*a*) additionally illustrates the tip and cut carrier 100 positioned along shafts 104 and 105 which are located parallel to respective left and right rods 26,28. Tip and cut carrier 100 provides the support for tipping assembly 300 that applies heat to a specific location of the suture material, and also provides support for the cutter assembly 200 that cuts the suture material. In the preferred embodiment, vertical movement of the tip and cut carrier 100 is accomplished by cranking handwheel 108 shown in FIG. 2(*b*). Other embodiments may implement a computer controlled servo motor to vertically register the tip and cut carrier 100 prior to cutting the material.

As illustrated in FIG. 2(*b*), cranking handwheel 108 actuates a gearbox 113 that rotates chain drive sprocket 114. The gearbox 113 is mounted on a gearbox mounting bracket 122 which, in turn, is mounted to frame member 99. A cable chain 115 is engaged with chain drive sprocket 114 to actuate movement of the tip and cut carrier 100 as shown in FIG. 2(*b*). The cable chain 115 also engages chain idler sprockets 118 and 119 which are rotatably mounted to upper tensioner pulley bracket 121 and lower tensioner pulley bracket 123, respectively. The vertical positioning of tensioner pulley brackets 121,123 may be adjusted to vary the slack in cable chain 115. Cable chain 115 also engages chain idler sprockets 127 and 129 which are suitably mounted on left side rail 22. As shown in FIG. 2(*a*), the back 111 of tip and cut carrier 100 is clamped to cable chain 115.

Both the stroke of the grippers 30,32 and the positioning of the tip and cut carrier 100 along drawing tower 20 dictates the length of the material that will be cut. For instance, as shown in FIG. 2(*a*), proximity sensors 73,74, and 75 are positioned vertically at different heights along the drawing tower 20 to enable predetermination of the length of suture material to be cut. Specifically, the locations of the proximity sensors 73,74, and 75 sense the positioning of the tip and cut carrier 100 as controlled by handcrank 108 in order to notify the control system 80 to change the reciprocating travel of grippers 30,32. Also as shown in FIG. 2(*a*), proximity sensor 70 is mounted at a position along the right side rail 24 to verify that right gripper 32 has reached a desired position at the upper end of the tower 20 and notify the control system 80 and servomotor 38 accordingly. Likewise, a proximity sensor (not shown) is mounted at the desired height along the left side rail 22 to verify that left gripper 30 has reached its desired position at the upper end of the drawing tower 20.

Preparing a predetermined length of (suture) material for cutting and swaging is accomplished as follows:

FIG. 2(*a*) shows suture material 55 being drawn by first gripper means or right gripper 32 from a king spool 50. In an alternative embodiment, the spool may be motor driven in which case a dancer assembly 59 may be provided to control the tension of the material as it is being fed. As shown in FIGS. 2(*a*) and 3(*b*), the lead gripper (gripper 32) grips the suture material 55 in the above-described manner just slightly below its tipped end 58.

To feed the indefinite length suture material up the length of the drawing tower, the suture material 55 is first manually threaded through eyelet 56 and through optional knot detector 57 which senses any sudden change in the thickness of the suture material. Detection of a knot in suture material 55 will trigger the control system 80 to discard the cut strand of material at a subsequent operation. Additionally, the suture material may be threaded within a tensioning (or dancer) assembly 59 which comprises a plurality of vertically spaced apart cones 23 each of which may be positioned laterally to increase or decrease the tension of the suture strand 55 as shown generally in FIG. 3(*a*).

The suture material 55 is then advanced over pulleys 35*a* and 35*b* and further around pulley 112 which is mounted on the lower portion of tip and cut carrier 100 that is illustrated near the center of the tower as shown in FIG. 2(*a*). Note that the lower threading pulley 35*b*, guide pulley 112, left gripper 30 and right gripper 32 are vertically aligned so that the cutter assembly 200 will always cut horizontally across the strand of material as will be discussed in detail below.

Under the control of the control system computer 80, the right servo motor 38 is enabled to drive the lead (right) gripper vertically along right rod 28 to register the tip of the indefinite length suture strand 55 for positioning within the suture receiving opening 29 of a precisely oriented surgical needle shown engaged by the multi-axis gripper 155 at the swaging assembly 400 located at the top of the drawing tower 20 as shown in FIG. 3(*b*). To accomplish this, the lead gripper servomotor advances the lead gripper for a long stroke distance, which may range from 12 inches to 36 inches depending upon the length of said suture strand desired, but is 16.1 inches in the preferred embodiment. The long stroke moves gripper 32 from a home position above the tip and cut carrier 100 and below the cutter assembly 200, to the position slightly below swaging assembly 400 as shown in FIG. 2(*a*).

Simultaneous with the positioning of the lead gripper 32 during the long stroke, the other servomotor, for e.g., servomotor 36, positions the alternate gripper, for e.g., left gripper 30, along left rod 26 at the home position preferably above the tip and cut carrier 100 and below the position of the cutter assembly 200 as shown in FIG. 2(a). It is understood that the top or right gripper is gripping the material 55 at all times during the long stroke, while the bottom or left gripper is in its open position and not gripping. The process of advancing suture material 55 by alternating grippers at each cycle eliminates the recycle or return time for retaining the gripper to the original position. This makes faster machine speeds and hence, higher production rates possible.

To insert the tipped end 58 of the suture material within the suture receiving opening 29 of surgical needle 21, the lead gripper 32 again advances the suture material 55 for a short stroke distance of about 1.9 inches, so that the tipped end 58 will advance precisely within the suture receiving opening 29 of needle 21 for a swaging operation to take place at the swaging assembly 400.

As the tipped end 58 of the suture material is advanced during the short stroke distance, a tipped portion 78 of the material 55 that has been heated by tipping assembly 300, (explained hereinbelow), advances to a position slightly above the location of the left gripper 30 and adjacent the cutter assembly 200. Then, as the automatic swaging of the tipped end 58 to the surgical needle occurs at swaging assembly 400, the left gripper 30 (lower gripper) is actuated to grip the material 55 in the tipped portion 78, i.e., the portion of the suture material heated by tipping assembly 300 as shown in FIG. 2(a), and the cutter assembly 200 is actuated to cut the tipped portion 78 of the suture material 55 so that the left gripper 30 is now gripping an indefinite length suture strand 55 having a tipped end 58. Simultaneous with the engagement of left or bottom gripper 30, the top or right gripper 32 is actuated to release its grip on the definite length suture material.

Heater Assembly

As mentioned above, immediately after advancing the long stroke distance and prior to advancing the short-stroke distance, the lead gripper is temporarily halted so that a portion of the suture material 55 may be heated (tipped). Heating of the suture under tension and the subsequent cooling thereof will stiffen the material and aid in the positioning and subsequent swaging of the tip of the material within the confines of the surgical needle. The operation of the tipping assembly 300 mounted on tip and cut carrier 100 will now be explained as follows:

As shown in FIG. 8, the tipping assembly 300 is essentially an oven comprising a heat exchanger unit 305 that heats the air in the heater cavity 306. When a pulse of incoming air is provided to the heat exchanger input 307, the heated air is displaced and it provides a pulse of heated air to a vertical cylindrical cavity 310 as shown in FIG. 2(a). As shown in FIG. 8 the heated air is forced through horizontal orifice 315 for a predetermined duration so that the length of suture material 55 suspended in tension through vertical cavity 310 will be heated. The control system computer 80 controls the duration of the heat pulse so that the material is adequately heated and will have sufficient time to cool before the cutting operation. Preferably, the tipping assembly 300 is located at a position that is located slightly below the bottom or left gripper. As mentioned above, this is required so that when the suture material 55 is advanced the short stroke distance, the tipped portion 78 of material 55 will advance a corresponding distance so that it may be cut by cutter assembly 200. This ensures that the bottom gripper, e.g., left gripper 30, will grip the material having a new tipped end 58 for the next suture draw/insert cycle.

It should be understood that various other "tipping" technologies will work depending upon the type of suture material that is being processed. For instance, when VICRYL® and VICRYL®-like suture materials are used, tensioning of the strand, in addition to hot air application to a strand will enable the surface thereof to be melt and recast to form a stiffened tip. The application of tension in addition to a heated, grooved, die for forming the tip diameter of VICRYL® suture materials may also be used; however, the use of a die to form the tip diameter, requires closer control of the strand location to ensure that a tip gets into the die groove for every cycle. For wax-impregnated suture materials like silk, the application of tension only at predetermined locations, will form a stiffened portion of the suture strand at those locations. Another tipping method for use with braided suture materials, involves applying and penetrating the braid with a dilute resin material such as General Electric's VITEL® having a high solvent content, and quick drying the applied portions with hot air while maintaining tension of the suture strand materials to form a stiffened tip thereof.

Cutter Assembly

Figure 5:
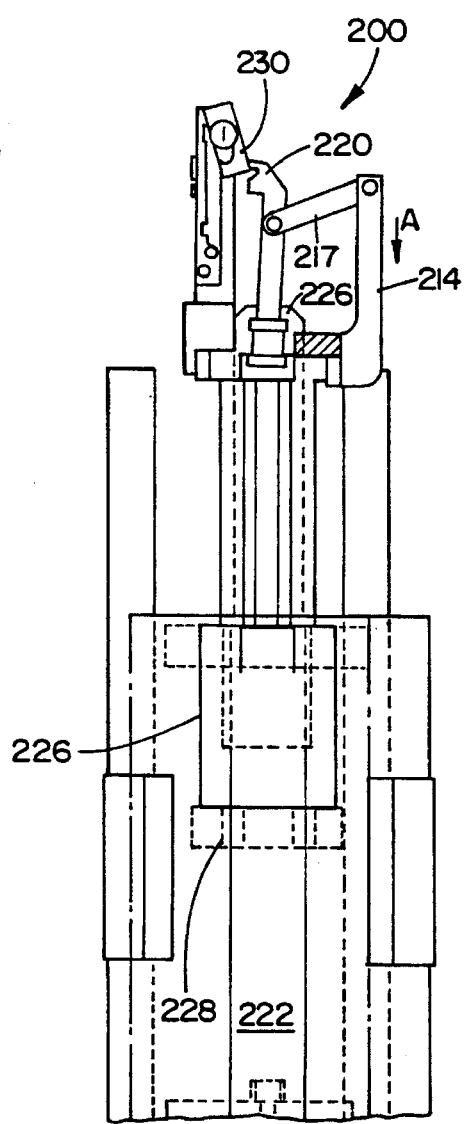
FIG. 5 is a detailed top view of the cutter assembly 200 for cutting material in the instant invention.

FIGS. 5–7 illustrate in detail the cutter assembly 200 which is suitably mounted to the tip and cut carrier 100 as shown in FIG. 2(a). As shown in FIG. 6, the cutter assembly comprises overcenter linkage 214 having a link arm 217 pivotally connected at one end thereof. A pivotal locator arm 220 is fixedly connected to link arm 217 at a second end thereof and is illustrated in FIG. 6 as substantially transverse thereto. The other end of locator arm 220 is pivotally connected to a stationary guide mechanism 226. Note, that all pivotal linkages described herein are simple pin linkages, the actuation of which creates the dwell moment for cutting the suture strand and obviates the need for complicated cam, slots, and sliding mechanisms.

As shown in FIG. 6, the stationary guide 226 is located in a plane perpendicular to the drawing axis of the suspended strand of material 55, and is located a distance from the strand approximately equivalent to the length of locator arm 220. In addition, overcenter linkage 214, locator arm 220, and cutting blade 230 all lie in planes perpendicular to the drawing axis of the strand of material 55.

A retractable ball slide 228 is mounted on the stationary guide 226 and coupled to overcenter linkage 214 for moving the overcenter linkage 214 and blade 230 along the stationary guide 226 in the direction indicated by arrow "A" in FIG. 5 from a cutting position to a retracted position shown in FIG. 6. As the ball slide 228 moves overcenter linkage 214 to a retracted position, the locator arm 220 is pivoted away from the strand 55 and the blade 230 is retracted. Thus, when the cutter assembly 200 is in the retracted position prior to cutting of the strand and immediately thereafter, the blade 230 and locator arm 220 do not interfere with the reciprocating motion of the grippers 30,32 along the drawing tower 20, nor do they come in contact with the suspended strand 55. In the preferred embodiment, pneumatic air cylinder 222 enables reciprocating movement of the ball slide 228 along stationary guide 226 as shown in FIG. 5.

When cutting the strand of material 55, the retractable ball slide 228 reciprocates in the direction toward the strand 55 indicated by arrow "B" in FIG. 6 to bring the overcenter linkage 214, cutting blade 230 and locator arm 220 to the cutting position shown in FIG. 7. As the overcenter linkage 214 moves to the cutting position, the link arm 217 translates the movement of the ball slide 228 into pivotal movement of the locator arm 220. Locator arm 220 is provided with a V-shaped support notch 223 which functions to engage and position the strand of material 55 to be cut as the arm is pivoted into the cutting position. The V-shaped notch also functions to support the strand on two sides of the strand 55 while it is being horizontally cut on a third side. This enables clean, broom-free cuts especially of multi-filament suture material, which has a tendency to form a broom end when the strand is under tension and is cut by scissors, or, when the multifilament strand is sliced and otherwise, not properly supported.

The cutting blade 230 of cutter assembly 200 is fixedly mounted to reciprocating ball slide 228 at a slight angle relative thereto and in a plane parallel with that of the locator arm 220. In the preferred embodiment, a single action by the pneumatic air cylinder 222 will enable movement of the reciprocating ball slide 228 along stationary guide 226. This consequently enables pivoting of locator arm 220 from its retracted position (FIG. 6), so that V-shaped notch 223 supports the strand 55 at two sides thereof while a third side of the strand bears upon the cutting edge of blade 230 as the blade moves towards the supported strand 55 traversing the drawing axis thereof. Thus, the strand 55 is cut in a dwell moment of the locator arm after the locator arm 220 has pivoted in the direction toward the blade 230 to the cutting position shown in FIG. 7. The blade 230 slices the strand of material while it is held stationary by locator arm 220 by virtue of the angled orientation of the blade with respect to the axis of reciprocation illustrated in FIGS. 6 and 7. In the preferred embodiment, the slice ratio is 1:1, with the blade 230 angled at approximately 45 degrees relative to the axis of reciprocation, so that the strand 55 is cut an amount equivalent to the distance the blade 230 traverses the drawing axis.

Swage Dial/Multi-axis Gripper

Figure 9:
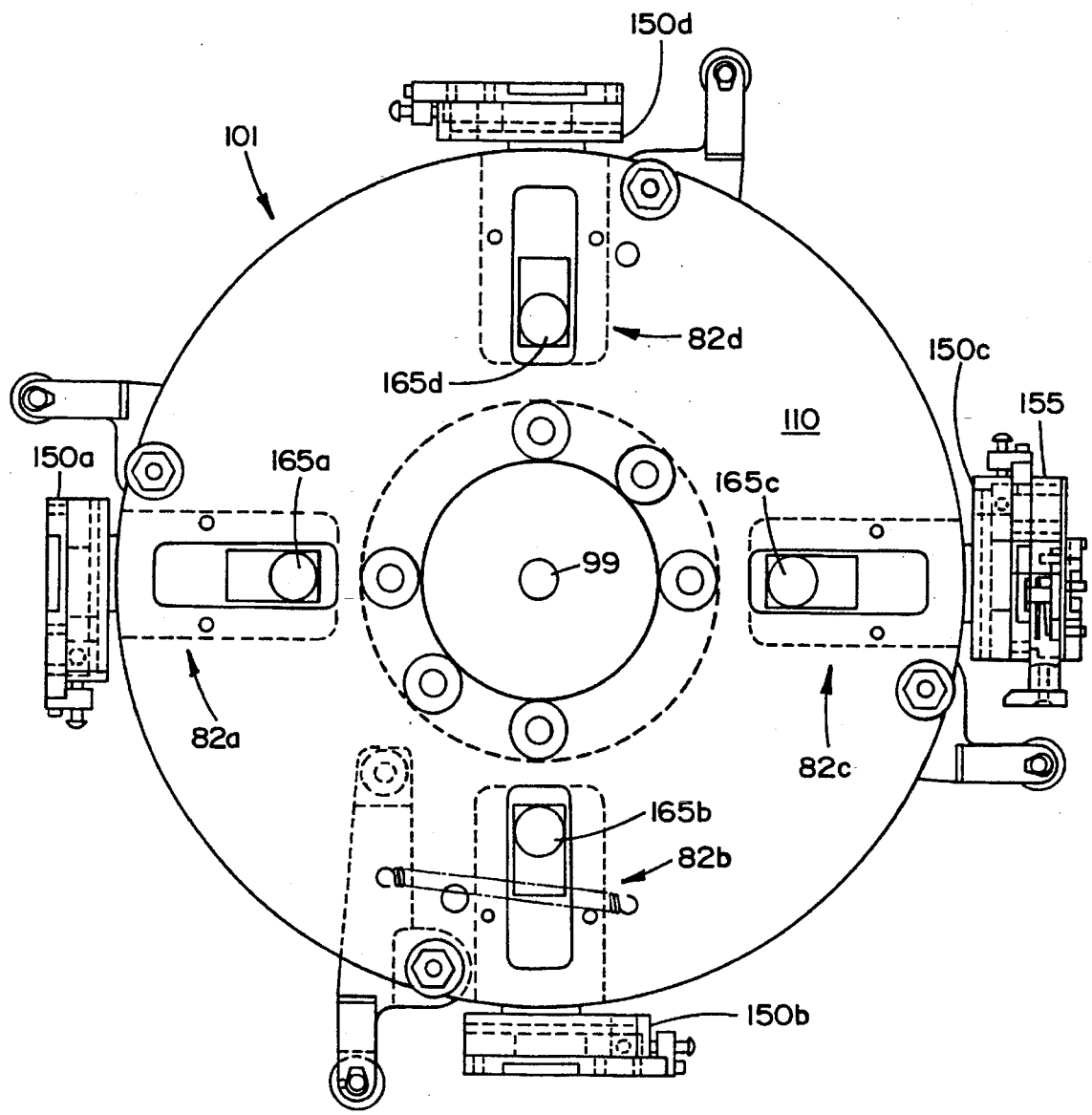
FIG. 9 is a top view swage dial assembly 101 having four multi-axis gripper stations.
Figure 10A:
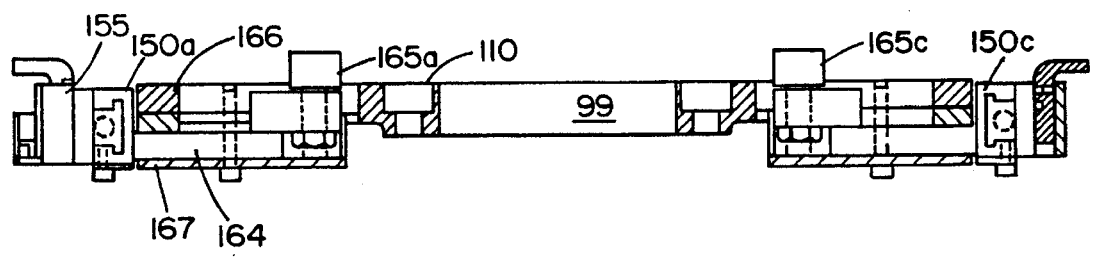
FIG. 10(a) is cross-sectional view of the four station swage dial assembly 101 showing multi-axis gripper 155 in a retracted position.
Figure 10B:
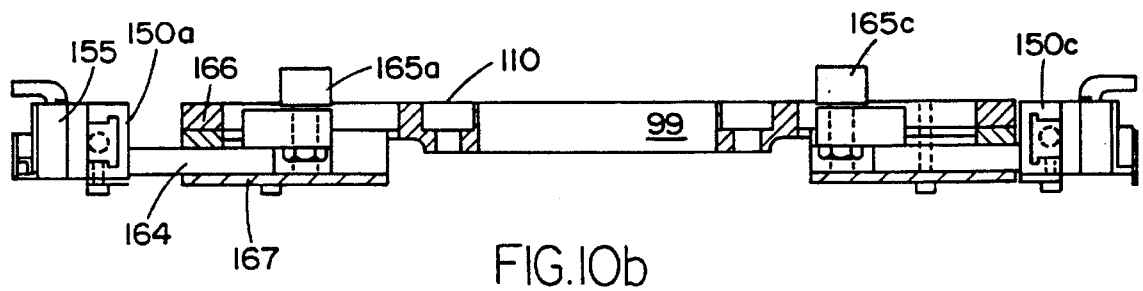
FIG. 10(b) is cross-sectional view of the four station swage dial assembly 101 showing multi-axis gripper 155 in an extended position.
Figure 11A:
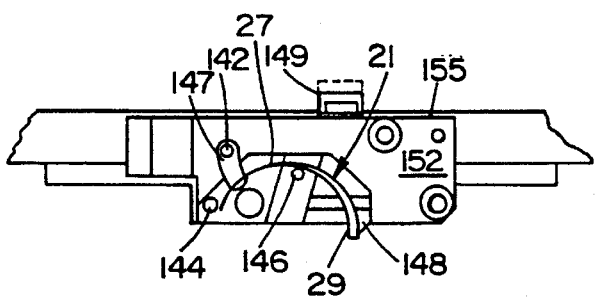
FIG. 11(a) is front face view of the multiaxis gripper 155 showing a surgical needle 21 in a relaxed engagement thereby, and additionally showing pin in a retracted position.

As illustrated in FIG. 9, the needle and suture swaging station includes a rotatable swage dial assembly 101 having four separate multi-axis gripper stations 82a,b,c,d where simultaneous operations are performed. The swage dial assembly 101 includes a swage dial 110 that is mounted to a rotatable central hub 99 which rotates under the control of a control system computer 80. In the preferred embodiment, a reciprocating carriage is provided at each station of the swage dial assembly 101. For instance, as shown in FIG. 9, swage dial station 82a includes reciprocating carriage 150a, while station 82b includes reciprocating carriage 150b, station 82c includes reciprocating carriage 150c, and station 82d includes reciprocating carriage 150d. Mounted to each reciprocating carriage 150a,b,c,d for retractable movement therewith, is a multi-axis gripper 155, one of which is shown connected to reciprocating carriage 150c in FIG. 9. The multi-axis gripper 155 includes pins 142,146, and 148 as shown in FIG. 11(a) that retain the surgical needle 21 in a fixed position. When the multi-axis gripper 155 is in the retracted position shown in FIG. 10(a), the needle 21 is being indexed to a different station as the swage dial rotates; when the gripper 155 is in the extended position as shown in FIG. 10(b), the needle is in one of the active stations, such as the station where it is registered for automatic swaging. A description of the preferred embodiment of the multi-axis gripper 155 follows hereinbelow.

Figure 11B:
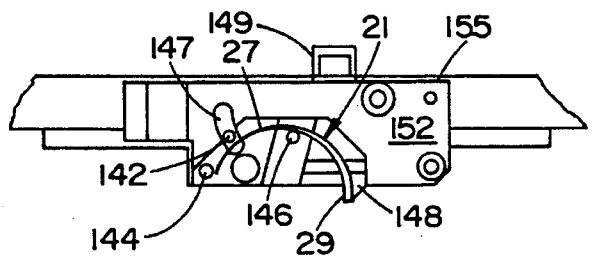
FIG. 11(b) is front face view of the multi-axis gripper 155 showing a surgical needle 21 in an engaged position therein.

As shown in FIG. 11(a), pins 142, 146, and 148 of the multi-axis gripper 155 extend perpendicularly from the gripper pin assembly 152 of the gripper to engage the arcuate portion 27 of needle 21, and to retain the needle in an oriented position. FIG. 11(b) illustrates pin 142 located along the outer arcuate portion of the needle 21, while pin 146 supports the pin at the inner arcuate portion 27 of the needle 21. The barrel portion of the needle 21 fits adjacent protruding stop 148 located on the gripper pin assembly 152 of the gripper 155 as shown in FIG. 11(b). The location of the stop 148 may be adjusted to accommodate the engagement of different size surgical needles. In the preferred embodiment, the gripper pin assembly 152 is replaceable with other gripper pin assemblies having the stop 148 positioned to accommodate different sized surgical needles. Note that another pin, such as pin 144 shown in FIGS. 11(a) and 11(b) may be provided for further support of the needle when in a relaxed position upon the multi-axis gripper.

Figure 11C:
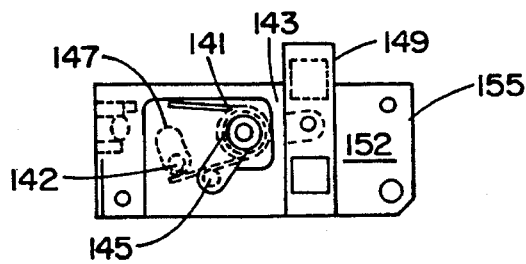
FIG. 11(c) is a hidden view of the actuating mechanism used to release the grip of the needle on the multi-axis gripper.

The three pin engagement configuration shown in FIG. 11(b) ensures that the needle 21 will not be displaced when the swage plate 110 is rotating, or, when the multi-axis gripper 155 is being retracted or extended. In the preferred embodiment, pin 142 is spring loaded and is retractable within guide 147 to release its grip of needle 21 prior to swaging thereof. FIG. 11(c) illustrates plunger 149 connected to actuating lever 143 having a pin 145 mounted thereon and adjacent one leg of torsion spring 141. To retract pin 142 within guide 147 needle, the plunger 149 is depressed by a suitable lever or push rod to rotate lever 143 causing pin 145 to move torsion spring 141 into engagement with pin 142 to retract the same to the non-engaging and relaxed position shown in FIG. 11(a). When engaging the surgical needle 21 after swaging, pin 142 is biased back into the needle engaging position as shown in FIG. 11(b). Note in FIG. 11(a) that the barrel portion of needle 21 extends below the gripper pin assembly 152 of the multi-axis gripper 155. This enables pick up of the needle at a first station and placement of the suture receiving end 29 of the needle within the swage dies of the swaging assembly as will be explained below.

Figure 12A:
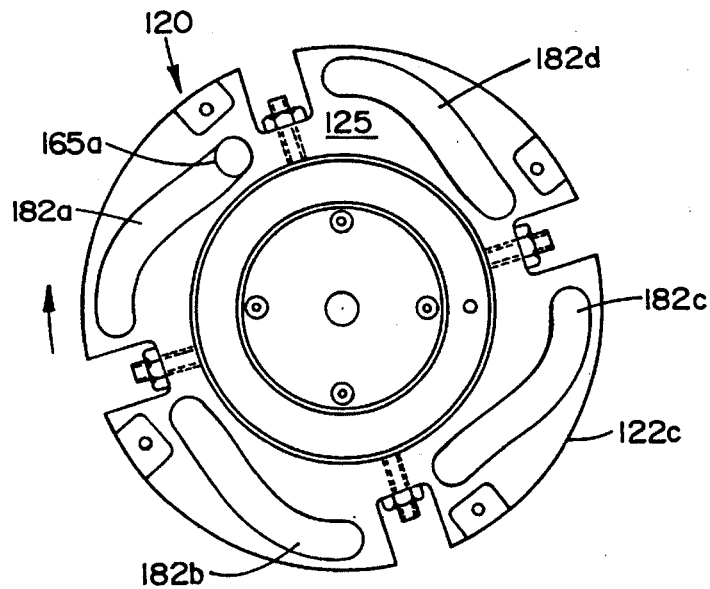
Figure 12B:
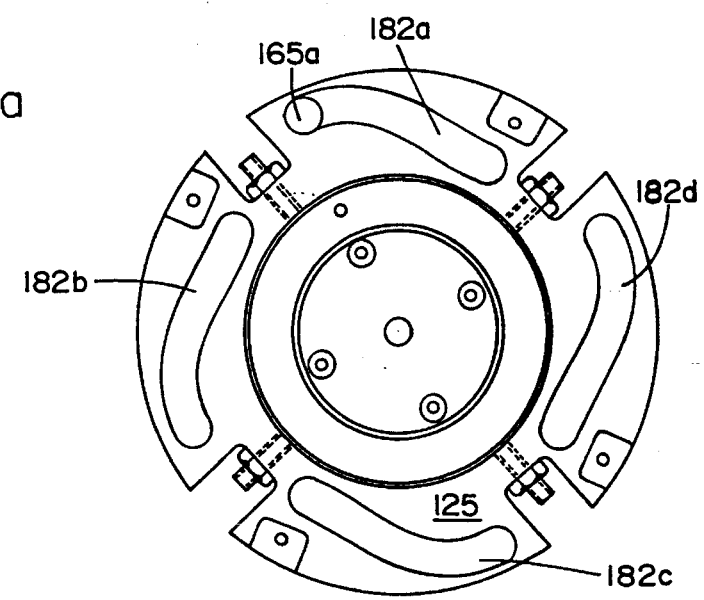
Figure 13:
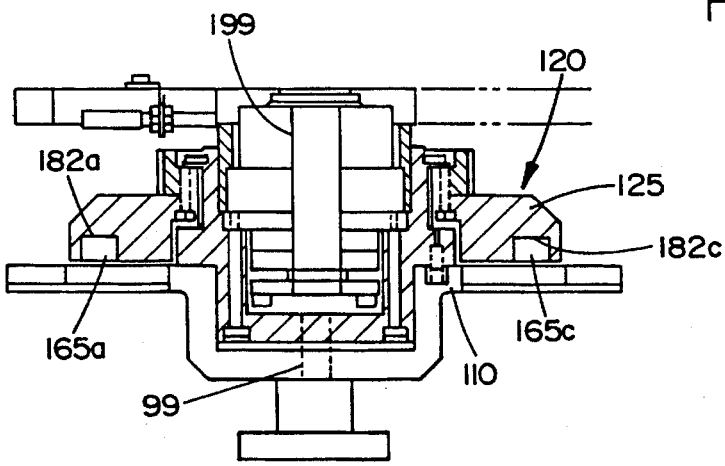
FIG. 13 is a cross-sectional view of the cam dial 125 mounted coaxial with the swage dial 110 for cooperative rotational movement thereof, and showing cam followers 165a,c in their retracted positions within respective cam tracks 182a,c.

The process for extending each multi-axis gripper 155 for suture insertion will now be explained. As shown in FIGS. 10(a) and 10(b), each cam follower 165a(b,c,d) is mounted to a cam slide 164 at one end of the reciprocating carriage 150a(b,c,d), and the multiaxis gripper 155 is connected to the cam slide 164 at the other end. Cam slide 164 is slidable within stationary guides 166,167 and is adapted for reciprocal movement when the cam follower 165 is actuated. In the preferred embodiment shown in FIG. 12(a), cam follower 165 is a roller that fits within cam tracks of a rotatable cam dial assembly 120. Cam dial assembly 120 is shown in FIG. 12(a) as comprising a cam dial plate 125 having four cam tracks 182a,b,c, and 182d which correspond to a swage dial stations 82a,b,c, and 82d, respectively. Each cam follower 165 is positioned within each respective cam track at each station for movement therein. For instance, as shown in FIG. 13, cam follower 165a is positioned within cam track 182a and cam follower 165c is positioned within cam track 182c. Also in FIG. 13, cam dial 125 is positioned above swage dial 110 and mounted coaxial therewith. The cam dial 125 is rotatable about a central shaft 199 and controlled by a separate rotary indexing transmission (not shown) so that it may rotate separately from the swage dial plate 110. FIG. 12(a) shows cam follower 165a in a first retracted position within the cam track 182a. When in this position, reciprocating carriage and consequently multi-axis gripper 155 are in their retracted position as shown in FIG. 10(*a*) discussed above. To extend the multi-axis gripper 155 in place at its respective station, the cam dial plate 125 is rotated in the clockwise direction indicated by the arrow in FIG. 12(*a*) for approximately 45–55 degrees relative to swage dial plate 110, forcing cam follower 165a in its cam track 182a to move toward the periphery of the dial as shown in FIG. 12(*b*). Consequently, the cam slide 164, reciprocating carriage 150a, and the multi-axis gripper 155 move to the extended position as shown in FIG. 10(*b*) and discussed above. To move back to its retracted position, the cam dial 125 is rotated in the counter clockwise direction relative to the swage dial plate 110 for approximately 45–55 degrees, forcing cam follower 165a in its respective cam track 182a to move to its retracted position (FIG. 10(*a*)).

It should be understood that when cam dial plate 125 rotates with respect to swage dial plate 110, each multi-axis gripper 155 is either extended or retracted by its respective cam track. Thus, the system is designed so that all processes performed at each station occur simultaneously and for approximately the same duration of time when the multi-axis grippers are in their extended position, for e.g., for needle pickup, for needle swaging, or, for needle pull-testing. The timing of the system is operated under a control system, the description of which can be found in the above-mentioned copending patent application U.S. Ser. No. 08/181,607, entitled "Control System".

When the multi-axis gripper 155 is retracted, the needle engaged thereby may then be indexed to a different station for further processing. To index the needle to another station, both swage dial plate 110 and cam dial plate 125 are rotated together for approximately 90 degrees to position the multi-axis gripper at the next station. For example, when the cam dial plate 125 and the swage dial plate 110 are simultaneously rotated 90 degrees counterclockwise in FIG. 13, the gripper 155 that had received the needle at station 82a is now indexed to the position corresponding to station 82b for swaging a suture thereto. After swage dial plate 110 stops rotating, cam dial plate 125 is rotated an additional amount to cam the four multi-axis grippers to the extended position. Similarly, after swaging, the cam dial plate 125 and the swage dial plate 110 are simultaneously rotated counterclockwise so that the armed needle at station 82b is conveyed to the position corresponding to station 82c for pull-testing thereof. The operations performed concurrently at each station about the swage dial increases throughput to provide an output of pull-tested armed surgical needles at a rate of approximately 60 per minute in the preferred embodiment.

Swaging Assembly

The swaging operation taking place at the swaging station will now be described. FIGS. 3(*b*)–3(*g*) illustrate the multi-axis needle gripper 155 and swaging and suture alignment dies shown in various stages of the suture insertion and needle swaging sequence. This sequence, and the interaction of the dies in relation to each other, the needle, and the insertion of the suture, accomplish the insert and swage function with minimal parts and simple motions.

Figure 15A:
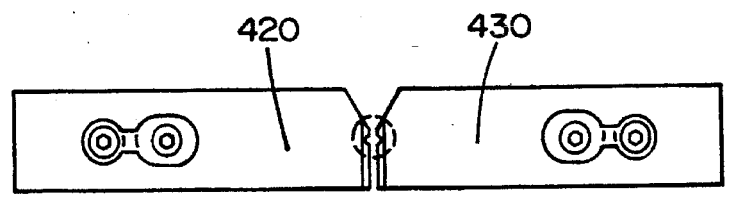
FIG. 15(a) is a detailed top view of the swage dies 420,430 of the swage assembly showing the recesses 434, 435 formed in the swage die opening 432 located therebetween.
Figure 15B:
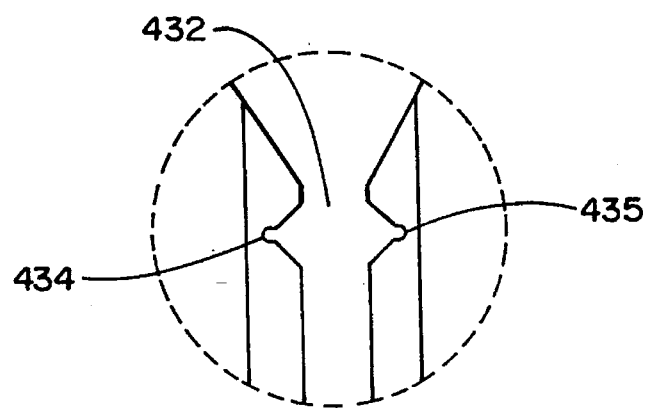
FIG. 15(b) is an enlarged view of the swage die opening shown encircled in FIG. 15(a).

After conveying the needle to swaging assembly 400, the multi-axis gripper 155 is radially extended from the swage dial in the manner described above to position the suture receiving end 29 of needle 21 between the funnel shaped die opening formed at the ends of two swage dies 420,430 as shown in FIG. 3(*b*) and the partial perspective view of FIG. 3(*c*). As will be explained in detail below, swage die 420 is fixed in position and swage die 430 is moved laterally toward the fixed swage die 420, as indicated by the arrow, to accomplish swaging of the suture receiving end of a needle placed therebetween. A funnel shaped die opening 432 having an exit diameter slightly larger than the diameter of the suture receiving end 29 of the needle is formed when the two swage dies 420,430 are positioned adjacent each other as shown in FIGS. 3(*e*) through 3(*g*). In the preferred embodiment shown in FIGS. 15(*a*) and 15(*b*), the ends of each of the swage dies 420,430 are provided with recesses 434,435, respectively, so that the metal deformation that occurs as a result of the swaging of the needle 21, does not result in metal flash or spurs at the suture receiving end 29 of the needle. Note that different sets of swage dies may be provided, depending upon the size (diameters) of the needles and sutures to be swaged.

To precisely position the suture receiving end 29 of needle 21 between the die opening formed at the ends of the two swaging dies 420,430, the movable swage die 430 is temporarily moved apart. In the illustration of the swaging assembly 400 shown in FIG. 14(*a*), swage die 430 is moved apart from the fixed swage die 420 by actuating air cylinder 445 which provides a force upon cylinder rod 443 to enable swage die operating lever 447 to pivot about screw 449 and pull moveable swage die 430 a predetermined distance away from the fixed swage die 420. In the preferred embodiment, lever 447 is biased by spring 431 so that the movable swage die 430 will return toward the fixed swage die by the spring restoring force when the pressure provided by the air cylinder 445 is terminated.

FIG. 3(*d*) shows die 420 in its fixed position, and moveable die 430 in its spaced apart position prior to receiving the surgical needle 21 presented by multi-axis gripper 155. Suture alignment die 425, containing suture guide funnel half 425b, is positioned under die 420, and free to slide laterally within limits. Alignment die 425 has a tang 425a that protrudes into cavity 420a formed within swage die 420. Compression spring 420c bears against the back wall of cavity 420a and tang 425a such that funnel die 425 slides forward until it is constrained by cavity wall 420b. In this position, it is forward of the center axis defined by the suture receiving end of the needle, and serves as a shelf 425c that helps assure suture receiving end 29 of needle 21 is in position for swaging. In this stage of the cycle, the parts are not positioned for suture insertion, and suture clamp 65a gripping suture 55 and stiffened end 58, are in dwell. Suture alignment die 426, containing funnel half 427, is fastened to swage die 430 by suitable fastening means, described in detail below, and travels with it to the open position shown.

While the swage dies 420,430 are apart, the multi-axis gripper 155 is extended to position the suture receiving end of needle 21 within the opening 432 as shown in FIG. 3(*d*) and FIG. 14(*a*). After positioning the suture receiving end 29 of needle 21 at the swage die opening 432, the swage die 430, and suture alignment die 426, are moved toward needle 21 with the resilient spring force present in spring 431 (FIG. 14(*a*)) that is sufficient to enable the die 430 to grip and locate the suture receiving end 29 precisely against fixed swage die 420 without deforming the cavity of the suture receiving opening 29 formed therein. Concurrently, needle retaining pin 142 in multi-axis gripper 155 is raised by downward external force on plunger 149, as described above, thereby releasing the needle so that its position is determined by the grip of swaging dies 420 and 430. The motion of dies 426 and 430 cause the face 426a of suture alignment die 426 to come in contact with the corresponding face 425c of suture alignment die 425. The resilient force causing this motion is forceful enough to compress spring 420c, and move funnel die 425 to the left, such that tang 425a is no longer in contact with cavity wall 425b. Dimensioning of dies 430 and 426 is such that this motion results in the formation of two funnel halves 425b and 427 defining a smooth conical shape that is coaxial with the suture receiving end 29 of needle 21. FIG. 3(e) shows the suture receiving end 29 being gripped by the swage dies 420,430 prior to suture insertion. Note that the exit diameter of the conically shaped funnel guide formed of funnel halves 425b and 427 is preferably equal to or greater than the diameter of the suture tipped end 58 and smaller than the diameter of the suture receiving end 29 of the needle 21, as shown in FIG. 3(f), so that the tipped end 58 of the suture strand may be easily inserted therein.

Figure 3A:
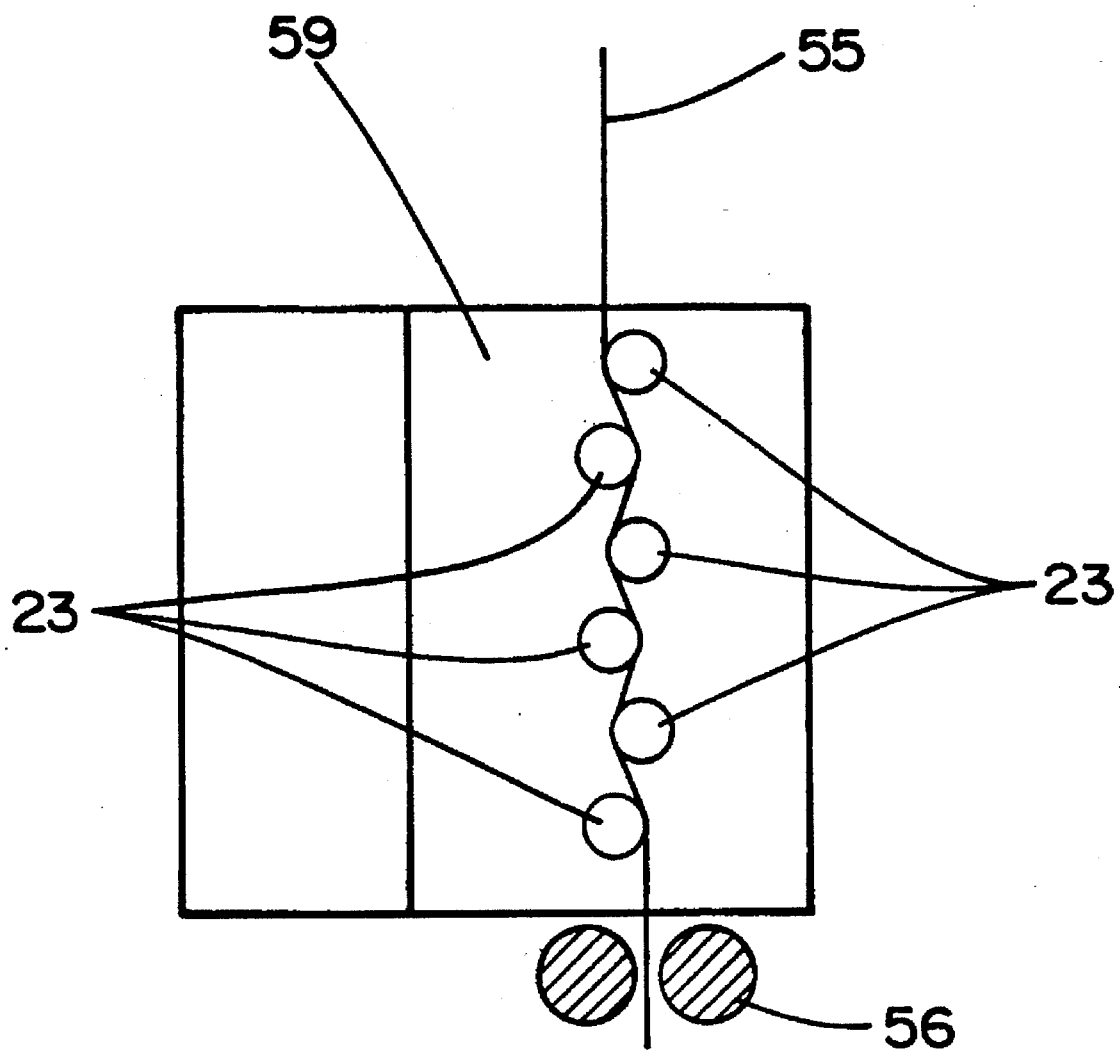
FIG. 3(a) is a detailed view of the tensioner assembly 59 for increasing or decreasing suture strand tension as desired.
Figure 3B:
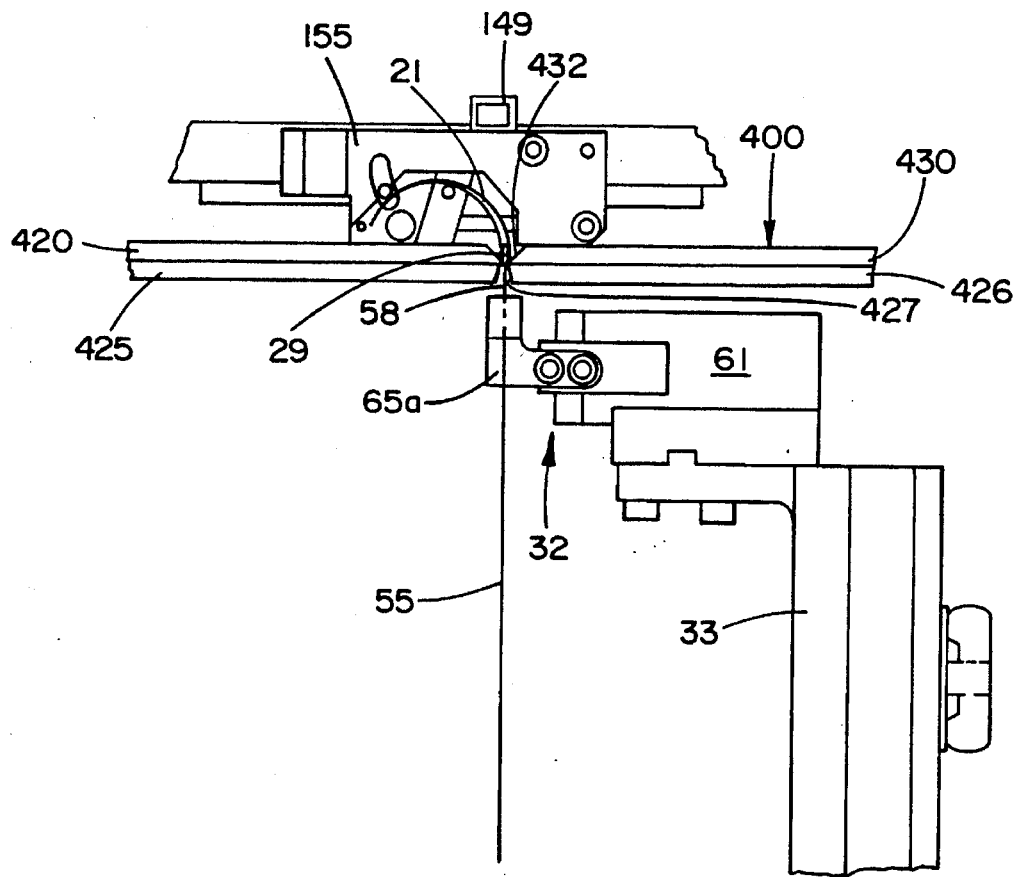
FIGS. 3(b)–3(g) illustrate the multi-axis needle gripper 155 and swaging and suture alignment dies shown in various stages of the suture insertion and needle swaging sequence.
Figure 3C:
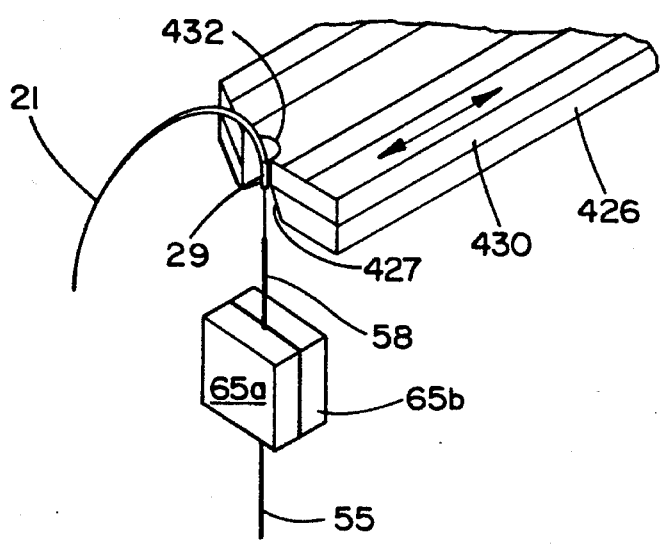
Figure 3D:
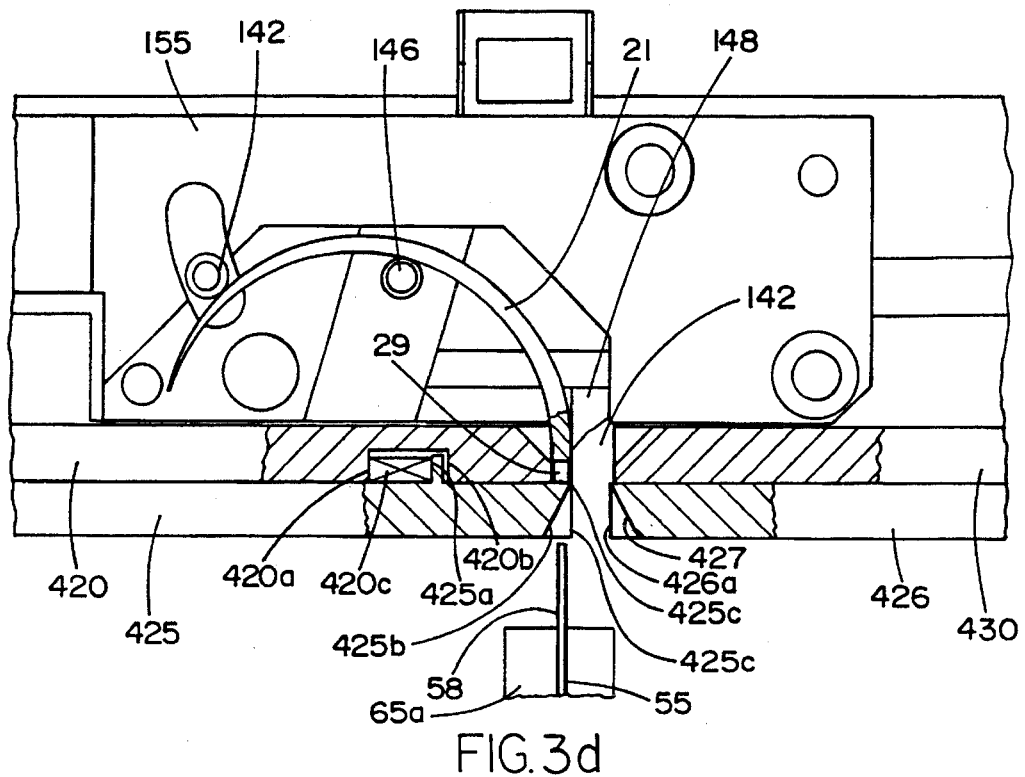
Figure 3E:
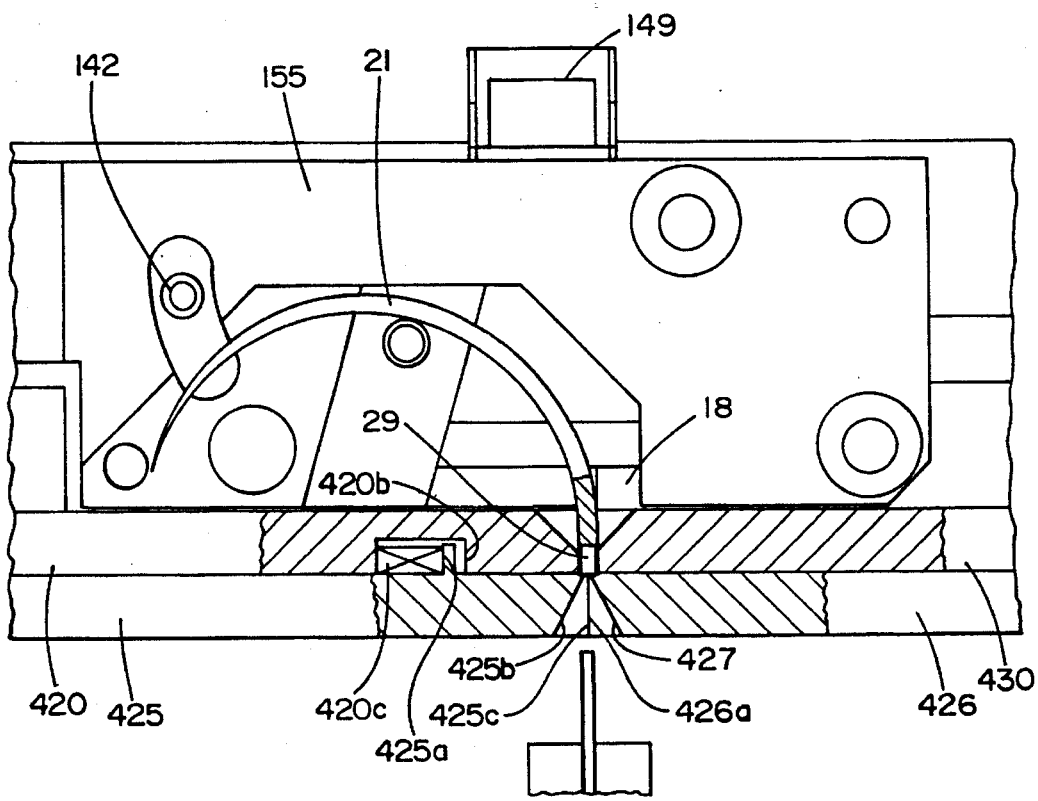
Figure 3F:
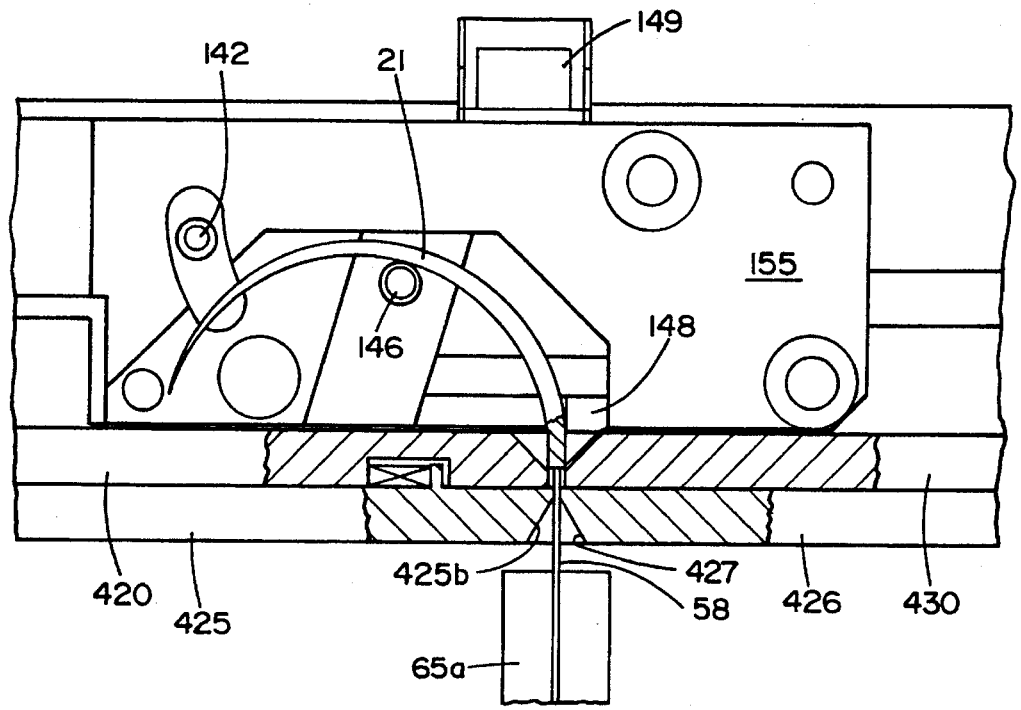

FIG. 3(f) shows suture gripper 65a moved vertically to the insertion position, which causes stiffened suture end 58 to enter funnel 425b and 427, and be guided into the suture receiving cavity 29 of needle 21 axially aligned therewith. Once the strand is inserted into the suture receiving end 29 of the needle (step 16) as discussed above, the automatic swaging of the suture receiving cavity occurs. In the preferred embodiment of the swaging assembly 400 shown in FIG. 14(a), a pneumatic air cylinder supplies air pressure to swage air cylinder 450 which actuates cylinder rod 433 that bears on lever 447 to thrust movable swage die 430 toward the fixed swage die to accomplish the swaging of the suture receiving end of the needle placed therebetween. Air pressure is supplied to the swage cylinder 450 via ports 451,452 under the control of the control system computer 80.

Figure 3G:
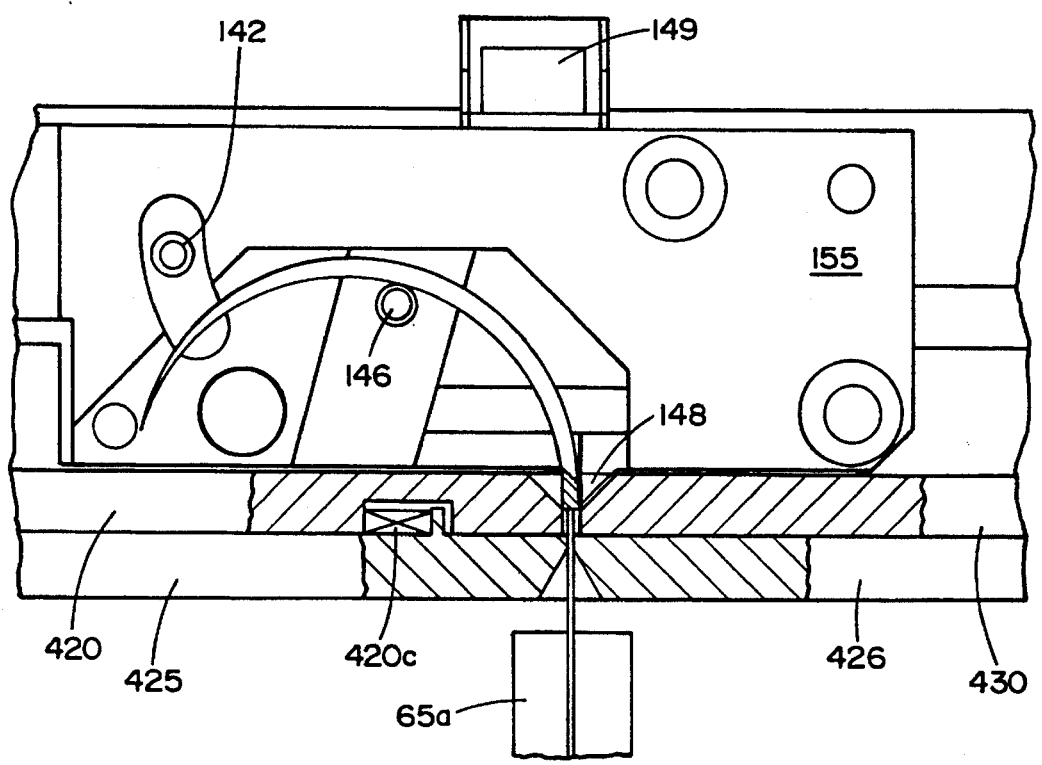

FIG. 3(g) shows the completed swage stroke. The swage die 430 has been driven to a fixed stop by the swage cylinder, which exerted sufficient force to deform the suture receiving end 29 of needle 21. As deformation takes place, suture alignment die 426 further displaces funnel die 425, causing additional compression of spring 420c. In the preferred embodiment, the moveable swage die 430 comes to an automatic stop by a swage stop mechanism herein described.

Figure 14A:
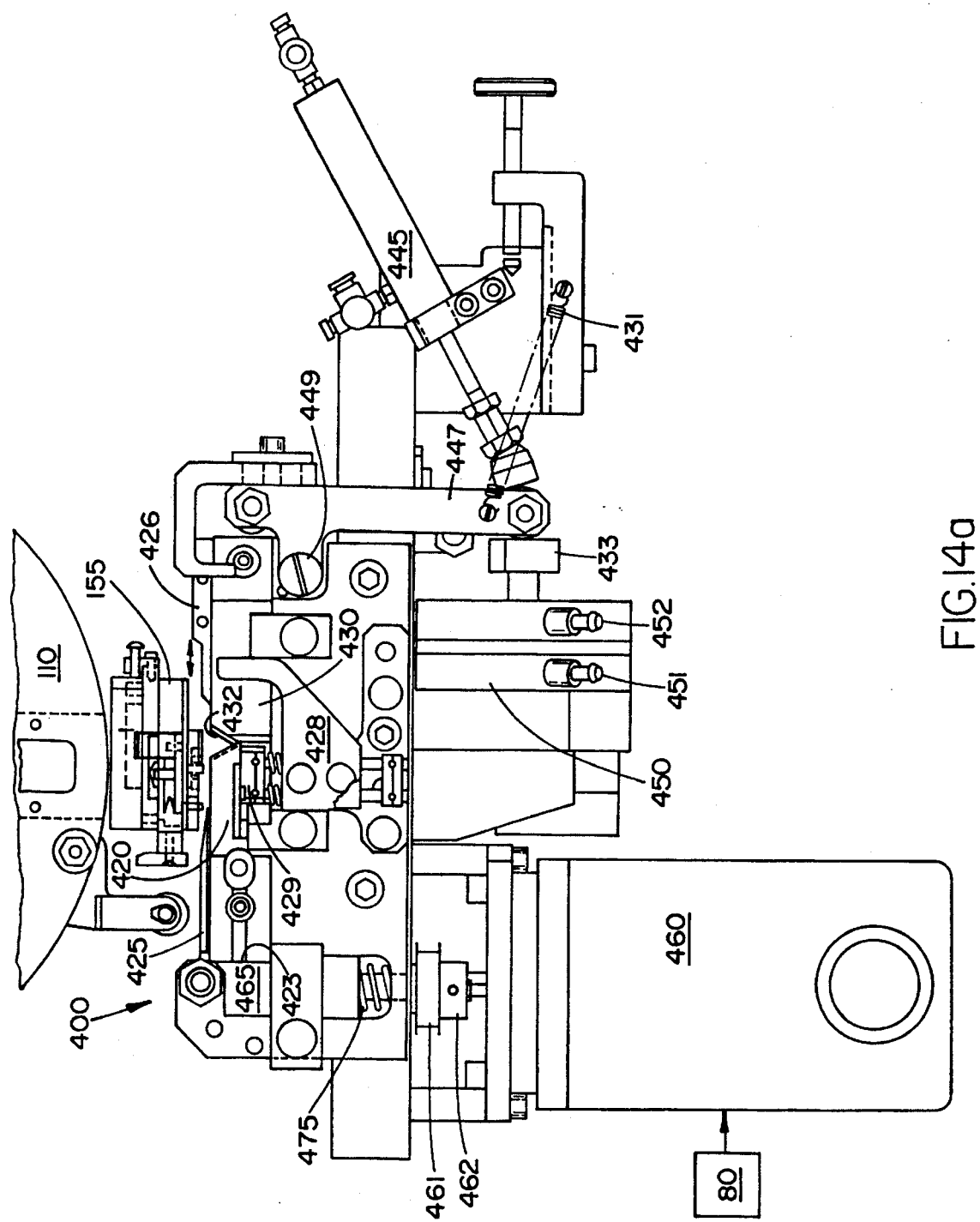
FIG. 14(a) is a top view of the swage assembly 400 of the instant invention.
Figure 14B:
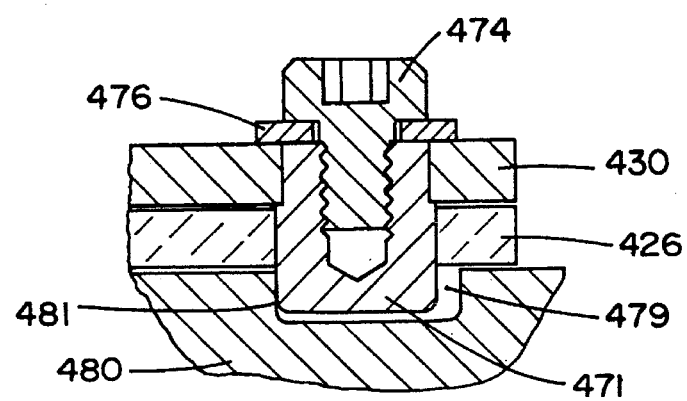
FIG. 14(b) is a detailed view of the swage stop mechanism for swage assembly 400.

As shown in FIG. 14(b), movable swage die 430 and suture alignment die 426 are mechanically held coincident to each other by shouldered post 471, the smaller diameter of which is a light press fit into the mating hole in die 430. Cap screw 474 with washer 476 retain the post in die 430. The larger diameter of post 471, below die 430, extends through a light press fit hole in funnel die 426 so that the right hand swage and funnel dies are linked to move together laterally during the swaging cycle. The lower portion of shouldered post 471 extends through funnel die 426 into groove 479, which is cross milled into swage assembly frame 480. When the swage stroke is performed, the swage cylinder drives this die assembly to the left until it is positively stopped by the lower portion of post 471 striking wall 481 of groove 479. This stalls air cylinder 450, so that the stroke of the moveable swage die assembly shown is always the same for repeating cycles of the machines.

In an alternative embodiment, both swage dies 420,430 may be movable towards each other to accomplish swaging. Furthermore, an adjustable swage stop mechanism for changing the swage stroke distance of one of the movable dies may be provided to further control the swaging pressure applied to the suture receiving opening.

As shown in the top view of FIG. 14(a), a needle fence assembly 428 is provided to ensure that the needle 21 does not tip or become misaligned when the needle is being swaged. The needle fence assembly 428 comprises a needle fence plate 429 whose distance from the swage die opening 432 is adjustable depending upon the size of the surgical needle to be swaged.

In the preferred embodiment, the degree of swage compression imparted on the needle, and resulting strength of grip by the needle on the suture, is adjusted by precise positioning of the fixed die 420. As shown in FIG. 14(a), servomotor 460 drives pulley 462 via timing belt 461 which rotates the swage adjust screw 475. The pitch of the swage adjust screw 475 is selected to move sliding wedge 465 a small distance. The swage die 420 has a complementary ramp angle 423 at the opposite end which bears on the wedge 465 to retract or advance the position of the swage die 420 a precise distance proportional to the movement of the sliding wedge. Thus, the rotation of the swage adjust screw 475 and motion of the sliding wedge 465, results in transverse movement of the swage die 420 to thereby finely adjust its fixed position. For example, when a larger suture is to be swaged to a needle, the position of the fixed swage die 420 may be moved further away from the suture drawing axis so that less swaging pressure is applied to the needle when the movable swage die 430 is thrust towards the fixed die to a stop. In the preferred embodiment shown in FIG. 14(a), the control system computer 80 will send the appropriate signals to automatically direct the servomotor 460 to adjust the position of the swage adjust screw 475, and hence, the position of the fixed die 420, in accordance with the pull-out test values of the needle-suture bond as measured downstream of the swaging station by an automatic pull-test system as explained in further detail in copending patent application U.S. Ser. No. 08/181,601, entitled "Needle and Suture Automatic Pull Test System" assigned to the same assignee of the present invention. Specifically, appropriate signals may be sent to automatically direct the servomotor 460 to adjust the rotational position of the swage adjust screw 475 in accordance with stored statistical results of the pull-testing occurring at the pull-test station. Automatic pull-testing of the armed needle is desirable to ensure that the upstream swaging dies are optimally positioned to avoid over-swaging the needle-suture bond and hence, preventing the likelihood of clip-off, and, to avoid under-swaging the needle-suture bond to prevent the chance of pull-out.

Immediately after the short stroke of the right or top gripper 32, the left gripper 30 secures the suture strand, and the suture material 55 is cut by the cutting assembly 200 in the manner described above and as indicated in step 17 in FIG. 1. As shown in FIG. 2(a), the cutter assembly 200 is positioned slightly above the left gripper 30 so that the indefinite length suture strand 55 will be gripped when the swaged strand is cut. Thus, the left gripper 30 is now gripping the suture material 55 with a tipped end 58 and it now becomes the lead gripper.

In the preferred embodiment shown in FIG. 2(a), a vacuum air flow is energized to pull the strand of material 55 toward the nylon screen 251 to more precisely locate the suture strand in the target zone of the cutter. After cutting of the indefinite length suture material 55, the tail end 58 of the length of suture material that had been swaged to the surgical needle is sucked into a large vacuum pipe 275, that is connected to a vacuum assembly (not shown) by vacuum hose 280 as shown in FIG. 2(a). The vacuum created in vacuum pipe 275 exerts a mild tension in the strand of material to keep the tail end from entanglement or coming into contact with the machinery. However, it is mild enough to allow the strand to be pulled out of the pipe 275 as the armed needle and suture are indexed for further downstream processes.

After swaging of the needle, the movable die 430 is again retracted by air cylinder 445 and the pin 142 of the multi-axis gripper 155 is actuated to engage the armed needle as described above. Subsequently, the multi-axis gripper 155 is retracted (step 18) to its position along the swage dial 101 for subsequent indexing to the next station, for e.g., pull-test station, or, for further processing (step 19).

The cycle continues at the swaging station with the left gripper becoming the top gripper and vertically drawing the suture material 55 along the height of the drawing tower 20 to position the next strand to be cut for insertion within the surgical needle. As mentioned above, the process of advancing suture material 55 by alternating grippers at each cycle eliminates the recycle or return time for retaining the gripper to the original position.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. A needle and suture threading machine for automatically threading and swaging a surgical needle having a suture receiving opening formed therein, said machine comprising;
   (a) a lead gripping means for gripping a suture strand from an indefinite length supply of suture material, said lead gripping means being reciprocally disposed along a common suture axis from a first position to a second position, said second position defining an insertion zone;
   (b) means for cleanly cutting said suture strand at said first position to create a suture strand of definite length gripped by said at lead gripping means, and a suture of indefinite length;
   (c) indexing means for positioning said needle between first and second swaging dies with said suture receiving opening aligned with said suture axis;
   (d) a funnel guide means positioned at said second position between a free end of said definite length suture strand and said suture receiving opening of said needle;
   (e) means for advancing said lead gripping means along said suture axis, from said first position to said second position, and for directing said free end to the suture strand through said funnel guide means and into the suture receiving opening formed in said needle; and
   (f) swaging means for advancing at least one of said first and second swaging dies toward the other to swage said needle about the suture strand of definite length and form a needle suture assembly.

2. The needle and suture threading and swaging machine according to claim 1, wherein said first swaging die is fixed in position and has an end thereof defining a portion of a swage die opening, and said second swaging die is movable and has an end thereof defining another portion of said swage die opening, wherein said second swaging die is positioned next to said first swaging die to form said swage die opening for receiving said needle.

3. The needle and suture threading and swaging machine according to claim 2 wherein said swaging machine further includes means for moving said second swaging die laterally away from said first fixed swaging die prior to positioning said needle within said swage die opening.

4. The needle and suture threading and swaging machine according to claim 3, wherein said moving means further moves said second swaging die toward said first swaging die to grip said needle placed therebetween.

5. The needle and suture threading and swaging machine according to claim 4 wherein said moving means includes spring biasing means to provide a force sufficient to move said second swaging die toward said first swaging die without deforming said suture receiving opening of said needle positioned at said swage die opening.

6. The needle and suture threading and swaging machine according to claim 5, wherein said moving means includes an air cylinder for supplying adequate force to move said second swaging die toward said first swaging die to accomplish swaging of said needle gripped therebetween.

7. The needle and suture threading and swaging machine according to claim 6, wherein said second swaging die is moved towards said first swaging die for a swaging stroke of a predetermined distance to accomplish said swaging.

8. The needle and suture threading and swaging machine according to claim 7, wherein said moving means includes stop means for terminating the motion of said second swaging die during said swaging stroke.

9. The needle and suture threading and swaging machine according to claim 3, wherein said swaging means includes fence means for maintaining the position of said needle within said swage die opening during the swaging thereof.

10. The needle and suture threading and swaging machine according to claim 3, wherein said advancing means for advancing said at least one gripping means is a servomotor operable under the control of a control system computer means.

11. The needle and suture threading and swaging machine according to claim 10, wherein said swaging means further includes means for adjusting the position of said first fixed swaging die to change the amount of swage deformation occurring to said suture receiving opening during swaging thereof.

12. The needle and suture threading and swaging machine according to claim 11, wherein said first fixed swaging die includes a wedge follower located at one end thereof, said means for adjusting the position of said first fixed swaging die including a wedge assembly positioned to move transverse to said wedge follower to laterally move said wedge follower and said first fixed swaging die in accordance with transverse movement of said wedge assembly.

13. The needle and suture threading and swaging machine according to claim 12, wherein said transverse movement of said wedge assembly is controllable by a servomotor means for rotating a swage adjust screw of a predetermined pitch, said rotation of said swage adjust screw being translated into linear motion of said wedge assembly.

14. The needle and suture threading and swaging machine according to claim 13 wherein said control system computer means determines and controls the optimum positioning of said first fixed swaging die to avoid over-swaging and underswaging said needle.

15. The needle and suture threading and swaging machine according to claim 14 wherein said control system computer means determines and maintains the optimum position of said first fixed swaging die in accordance with pull-out force values of said needle-suture assembly as measured downstream of said needle and suture threading machine.

16. The needle and suture threading and swaging machine according to claim 2, wherein said indexing means includes means for gripping said needle in an engaged state or releasing said needle.

17. The needle and suture threading and swaging machine according to claim 16, wherein said needle gripping means is movable between a first retracted position prior to positioning and surgical needle within said swage die opening, and a second extended position for positioning said needle within said swage die opening.

18. The needle and suture threading and swaging machine according to claim 17 wherein said needle gripping means includes a plurality of pin means for engaging said surgical needle at predetermined locations, one of said plurality of pin means being retractable between a first engaging position for engaging said surgical needle in a precisely oriented position, and a second non-engaging position for releasing said surgical needle from its grip thereof.

19. The needle and suture threading and swaging machine according to claim 18, wherein said needle gripping means includes means for retracting one of said plurality of pin means between said first engaging position and said second non-engaging position.

20. The needle and suture threading and swaging machine according to claim 1, wherein said funnel guide means includes a tapered opening having a suture exit diameter that is equal to or greater than the diameter of said suture strand and smaller than the diameter of the suture receiving opening defined in the needle.

21. The needle and suture threading and swaging machine according to claim 20 wherein said funnel guide means includes a first fixed suture alignment die having an end thereof defining a portion of said tapered opening of said funnel guide means, and a second movable suture alignment die having an end thereof defining another portion of said tapered opening of said funnel guide means, wherein said second movable suture alignment die is positioned next to said first fixed suture alignment die to form said tapered opening of said funnel guide means.

22. The needle and suture threading and swaging machine according to claim 21 wherein said funnel guide means includes a registration means for engaging said second movable suture alignment die with said second swaging die for concurrent movement therewith.

23. The needle and suture threading and swaging machine according to claim 1 further including means for stiffening a portion of said suture strand in a stiffening zone located adjacent said first position while said suture is under tension.

24. The needle and suture threading and swaging machine according to claim 23 further including bottom gripping means reciprocable along said suture axis from said first position to said insertion zone, wherein said definite length suture strand is supported at said free end at said insertion zone by said lead gripping means after cutting thereof, and said suture of indefinite length being gripped between said stiffening zone and said cutting means by said bottom gripping means.

25. A needle and suture threading machine for automatically threading and swaging a surgical needle having a suture receiving opening formed therein, said machine comprising:

(a) first and second gripping means for gripping and advancing a suture strand under tension from an indefinite length supply of suture material, each of said gripping means reciprocating along a common suture axis form a stiffening zone to an insertion zone;

(b) means for cutting said suture strand in said stiffening zone to create a suture of definite length supported by said first gripping means and a suture of indefinite length supported by said second gripping means;

(c) indexing means for positioning said needle between first and second swaging dies with said suture receiving opening aligned with said suture axis;

(d) a funnel guide means positioned in the insertion zone between a free end of said definite length suture and said needle, said funnel guide means having a registration means for aligning it with at least one of said swaging dies;

(e) means for advancing said first gripping means along the suture axis to direct the free end of the definite length suture through said funnel guide means and into the suture receiving opening formed in said needle; and (f) swaging means for advancing at least one of said first and second swaging dies to swaging said needle about the suture.

* * * * *

UNITED STATES PATENT AND TRADEMARK OFFICE
CERTIFICATE OF CORRECTION

PATENT NO. : 5,477,609
DATED : December 26, 1995
INVENTOR(S) : David DeMarest, et al.

It is certified that error appears in the above-indentified patent and that said Letters Patent is hereby corrected as shown below:

Column 3, line 21: after "pin" insert --147--

Column 15, line 36, Claim 1: delete "at"

Signed and Sealed this

Third Day of September, 1996

*Attest:*

BRUCE LEHMAN

*Attesting Officer*     *Commissioner of Patents and Trademarks*